United States Patent [19]

Ball et al.

[11] 3,975,946

[45] Aug. 24, 1976

[54] LIQUID CHROMATOGRAPHY SAMPLE MEASURING AND INTRODUCING APPARATUS

[75] Inventors: Dean M. Ball; Ronnie W. Camp, both of Norcross; Warren P. Hendrix, Lawrenceville; Clyde Orr, Jr., Atlanta, all of Ga.

[73] Assignee: Micromeritics Instrument Corporation, Norcross, Ga.

[22] Filed: Dec. 17, 1974

[21] Appl. No.: 533,611

Related U.S. Application Data

[62] Division of Ser. No. 446,293, Feb. 27, 1974, Pat. No. 3,932,067.

[52] U.S. Cl. .................. 73/61.1 C; 73/422 GC; 137/625.15
[51] Int. Cl.² .................. G01N 1/20; G01N 31/08
[58] Field of Search .................. 73/422 GC, 61.1 C; 210/198 C, 31 C; 137/625.15

[56] References Cited
UNITED STATES PATENTS

| | | | |
|---|---|---|---|
| 3,071,005 | 1/1963 | Skidmore | 73/422 GC |
| 3,114,393 | 12/1963 | Vlasic | 73/422 GC X |
| 3,122,168 | 2/1964 | Wright | 73/422 GC X |
| 3,223,123 | 12/1965 | Young | 73/422 GC X |
| 3,297,053 | 1/1967 | McKinney | 73/422 GC X |
| 3,475,950 | 11/1969 | Ferrin | 73/422 GC X |
| 3,683,701 | 8/1972 | Gunther et al. | 73/422 GC |
| 3,747,630 | 7/1973 | Hurrell | 73/422 GC X |
| 3,864,978 | 2/1975 | Stephens | 73/422 GC |
| 3,885,439 | 5/1975 | Stone | 73/422 GC |

FOREIGN PATENTS OR APPLICATIONS

| | | | |
|---|---|---|---|
| 1,318,788 | 1/1963 | France | 73/422 GC |

*Primary Examiner*—Donald E. Watkins
*Assistant Examiner*—Joseph W. Roskos
*Attorney, Agent, or Firm*—Jones, Thomas & Askew

[57] ABSTRACT

Sample introduction apparatus useful in liquid chromatography and including a valve body having at least one fluid passage of precisely defined volume to receive a sample material and having another fluid passage delivering carrier liquid to a liquid chromatograph. The valve body can be manipulated to place the precisely defined volume in the chromatograph fluid circuit, so that the sample contained within the volume is positively displaced into the chromatograph.

4 Claims, 15 Drawing Figures

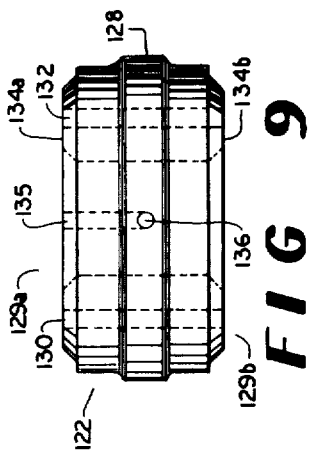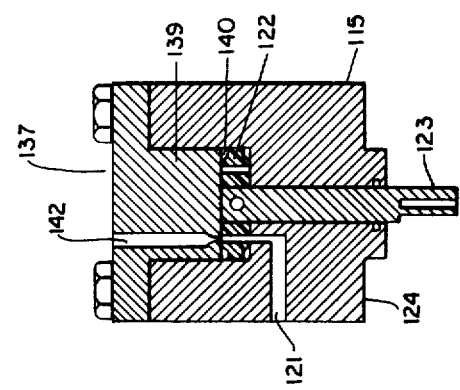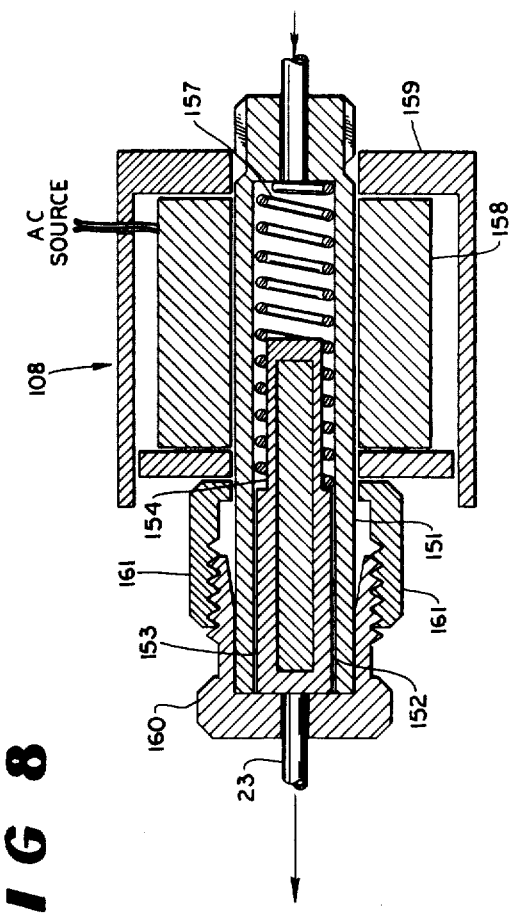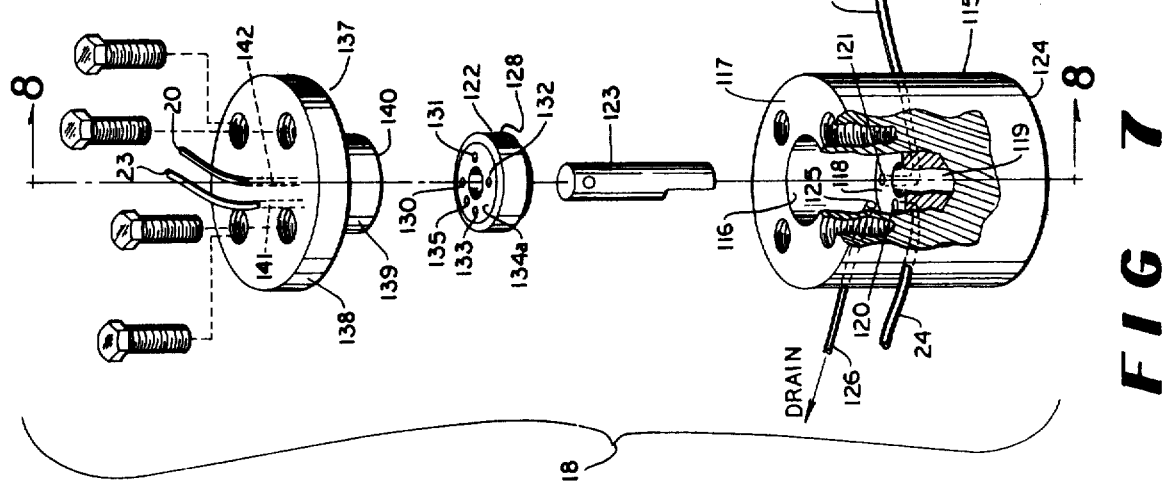

LIQUID CHROMATOGRAPHY SAMPLE MEASURING AND INTRODUCING APPARATUS

This is a division of application Ser. No. 446,293, filed Feb. 27, 1974 and now U.S. Pat. No. 3,932,067.

This invention relates in general to the field of chromatography and in particular to the field of liquid chromatography.

Chromatography is recognized by those skilled in the art as a procedure for analyzing a sample through the steps of passing the sample through a body of material and detecting the relative separations of various sample substances which occur during such passage. In the specific field of liquid chromatography, the sample undergoing analysis may typically be introduced into a carrier liquid which is passed through a chromatographic column containing material which adsorbs components of the liquid being analyzed. The extent to which these different components are adsorbed in the column is determined by a suitable detector connected to analyze the liquid effluent from the column.

Those familiar with the art of liquid chromatography are aware that it is essential to provide a flow of carrier liquid which is delivered to the chromatograph column at a desired constant rate of flow and which is free of any measurable pressure pulsations. The presence of pressure pulsations in the carrier liquid supplied to the chromatograph column can vary the rates of adsorption occurring within the column, and thus can provide a false indication of the adsorption of constituents in the sample being analyzed. These false indications amount to "noise" in the detector output, and this noise masks or otherwise obscures bona fide signals whose amplitude is not significantly greater than that of the pulsation-induced noise. The effective sensitivity of a liquid chromatograph can be increased, accordingly, by reducing the pressure pulsations in the carrier liquid.

Conventional constant-volume pumps, such as gear pumps and the like, are unsatisfactory for supplying carrier liquid flow in a liquid chromatograph. Such pumps, when used with the carrier liquids of low viscosity typically employed in liquid chromatography, fail to deliver the desired degree of pulseless operation, particularly at the higher portions of the pressure ranges employed in chromatography. Conventional reciprocating piston pumps deliver fluid output in pulses corresponding to piston strokes, and therefore have been found undesirable for supplying carrier liquid in chromatography applications. It has been proposed to utilize a single pumping stroke of a piston pump, suitably driven at a predetermined rate by a gear or screw drive mechanism, to provide the desired pulseless flow of carrier liquid. While this latter technique is acceptably free of pressure pulsations, the volume of carrier liquid and thus the time available for chromatographic analysis is obviously limited by the maximum practical volume of the cylinder associated with the piston pump. For this reason, the single-stroke piston pump has been less than satisfactory in applications where an extended duration of chromatographic analysis is desired.

An alternative approach attempts to use pulsation damping techniques to dampen the pulsations produced by prior-art pumps. This approach at best represents a compromise solution which does not yield the desired combination of pulseless operation for an indefinite duration of chromatograph operation.

A related problem in chromatographic analysis is the technique and apparatus used to introduce a precisely measured volume of sample fluid into the stream of pressurized carrier liquid. One prior art approach to the problem involves the use of a septum at an appropriate location in the carrier liquid conduit, permitting passage of a syringe which has previously been loaded with the desired measured volume of sample fluid. The septum requires frequent replacement, however, and it has been found in practice that the use of a septum is feasible only where carrier liquid pressure does not exceed about 1,000 psi. Another prior art approach to sample introduction is shown in U.S. Pat. No. 3,376,694, and involves the use of a sample loop conduit which is normally external of the carrier liquid conduit and which may be charged with the desired predetermined volume of sample fluid. A valve is then actuated to connect the external sample loop in series with the carrier liquid circuit, and the sample previously disposed in the sample loop is carried to a chromatograph column or other analytical apparatus. A significant drawback inherent in the external sample loop system is the presence of "dead volume", that is, volume containing only air or another gas instead of a liquid, introduced into the chromatograph circuit if the measured sample volume does not completely fill the external sample circuit. The existence of dead volume permits pressure variations and pulsations to occur in the system because of the compressibility of the gas in the dead volume, and thus introduces potential false readings into the chromatograph system. Other disadvantages include the limitation imposed by the sample loop on the minimum sample volume.

Accordingly, it is an object of the present invention to provide improved apparatus for use in liquid chromatography.

It is another object of the present invention to provide improved carrier liquid pumping apparatus for use in a liquid chromatograph system.

It is still another object of the present invention to provide pump apparatus for reducing or eliminating pressure pulsations in the flow of carrier liquid in a chromatograph system.

It is still another object of the present invention to provide improved apparatus for introducing a sample fluid into a liquid chromatograph system.

It is yet another object of the present invention to provide an improved detector apparatus for a liquid chromatograph.

The foregoing problems and other problems and shortcomings associated with prior art chromatographic apparatus are overcome by the present inventions, with other objects as well as many of the attendant advantages being apparent from the following description of the disclosed illustrative embodiment thereof, with reference to the drawings in which:

FIG. 7 is an exploded view, shown partially broken away, of a sample introduction valve according to a disclosed illustrative embodiment of the present invention;

FIG. 8 is a section view of an assembled valve as in FIG. 6;

FIG. 9 is an enlarged view of the rotor in the sample injection valve of FIGS. 7 and 8;

FIG. 10 is a section view of mixing apparatus used with the illustrative embodiment of FIG. 6;

Figure 1:
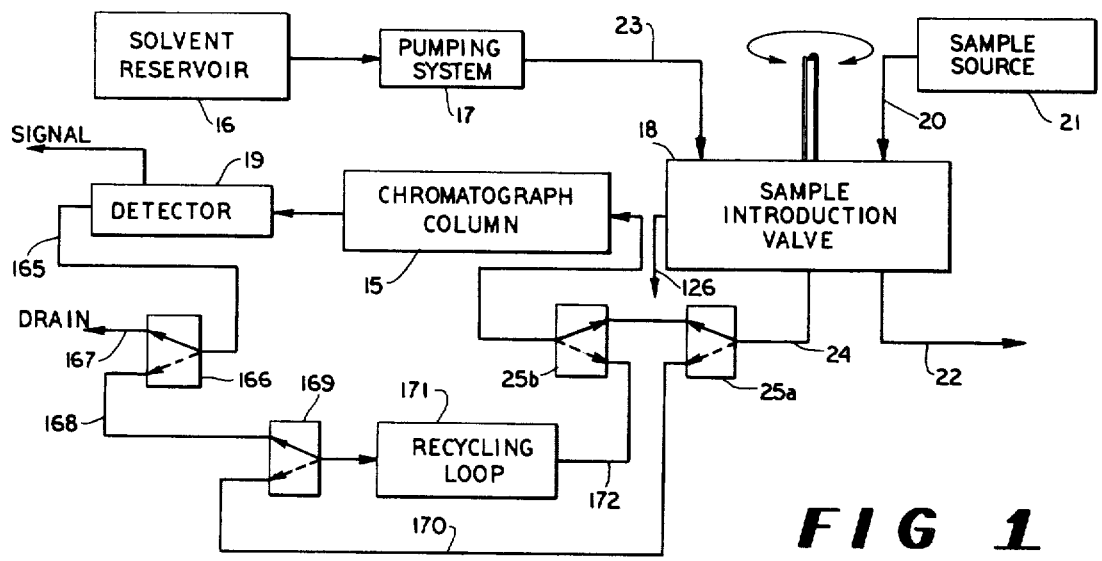
FIG. 1 is a block flow diagram showing a liquid chromatograph system according to a disclosed illustrative embodiment of the present invention.

Stated in general terms, the carrier liquid pump system of the present invention includes at least two pump means each of which is operable to supply a finite volume of carrier liquid at a flow rate determined by the rate of input drive to the pump means. One of the pump means is operated at a constant rate of input drive, so that the pump means supplies carrier liquid at a constant rate of flow. At a time before the first pump means completes delivery of its finite volume of carrier liquid, the input drive to the first pump means changes from a drive providing a constant flow rate output to a drive providing a constant pressure output. A second pump means commences to operate at this time, also supplied with input drive to provide the aforementioned constant pressure output. The particular output pressure is determined by the actual output pressure previously measured during constant flow rate operation. At a time after the second pump means has commenced delivering carrier liquid, drive input is removed from the first pump means and the drive input to the second pump means changes to a constant-rate drive. While only the second pump means is receiving input drive, the first pump means undergoes a reloading cycle permitting introduction of another finite volume of operating liquid to the first pump means for subsequent delivery. Carrier liquid delivered by the first and second pump means is supplied through a valve arrangement to a liquid chromatograph, and the aforementioned alternate operation of first and second pump means may be repeated indefinitely. A substantially pulsefree delivery of carrier liquid is accomplished through operation of the pump means in a constant-pressure mode during the transition between the two pump means.

Stated in general terms, the sample introduction valve of the present invention includes a movable valve member having at least one sample passage which is contained in the movable valve member and which has a volume equal to a desired volume of sample material to be introduced into a chromatograph. Another passage provided in the valve member passes a flow of carrier liquid to the chromatograph while the sample passage is aligned with a sample supply port to receive a quantity of sample material. The valve body is movable to place the sample-containing valve passage in series with the flow of carrier liquid to the chromatograph, whereupon liquid is displaced from the sample passage and is delivered to the chromatograph for analysis.

Stated in general terms, the sample recycling apparatus of the present invention is provided by a recycling conduit loop which is selectively connectable to receive and retain liquid outflow from the chromatograph. The liquid received in the recycling loop can be reintroduced to the chromatograph column for subsequent detailed analysis.

Included in the present invention is a mixing chamber which is useful for intermixing two or more carrier liquids, or other liquids occurring in discrete quantities in a conduit system. The mixing apparatus, stated in general terms, includes a piston reciprocally received in a cylinder of slightly greater diameter. The movement of liquid flowing between the piston and the cylinder wall, as the piston reciprocates, effectively intermixes the liquids.

Stated in general terms, the improved detector of the present invention includes a sample cell which is in heat transfer relation with the liquid to be admitted into the sample cell. Ultraviolet illumination passing through the sample cell is collected for application to a photosensitive device.

Pumping System

The pumping system of the present invention is more particularly shown with reference to the disclosed illustrative embodiment of apparatus including the invention and depicted in FIG. 1 as a liquid chromatograph system including a chromatograph column indicated generally at 15 and connected in a liquid flow circuit including a reservoir 16 to receive an appropriate solvent or other carrier liquid, a pulseless pumping system 17 as more particularly described below, a sample introduction valve 18 also as described below, the column 15, and a suitable detector apparatus 19. The detector 19 may be any type of detector apparatus known to the art for use in liquid chromatography, or may alternatively be an improved detector as described below. The sample introduction valve 18 is connected by a conduit 20 to a suitable sample source 21, and by a conduit 22 either to a vent to the atmosphere or to a source of suction, as will become more readily apparent below. The internal passages of the sample introduction valve 18 maintain a chromatograph liquid flow circuit from the pumping system 17, the conduit 23, through the valve 18, and onward through the conduit 24 and the recycle selection valves 25a, 25b, to the column 15. The purpose and selective function of the recycle selection valves is set forth below.

Figure 2:
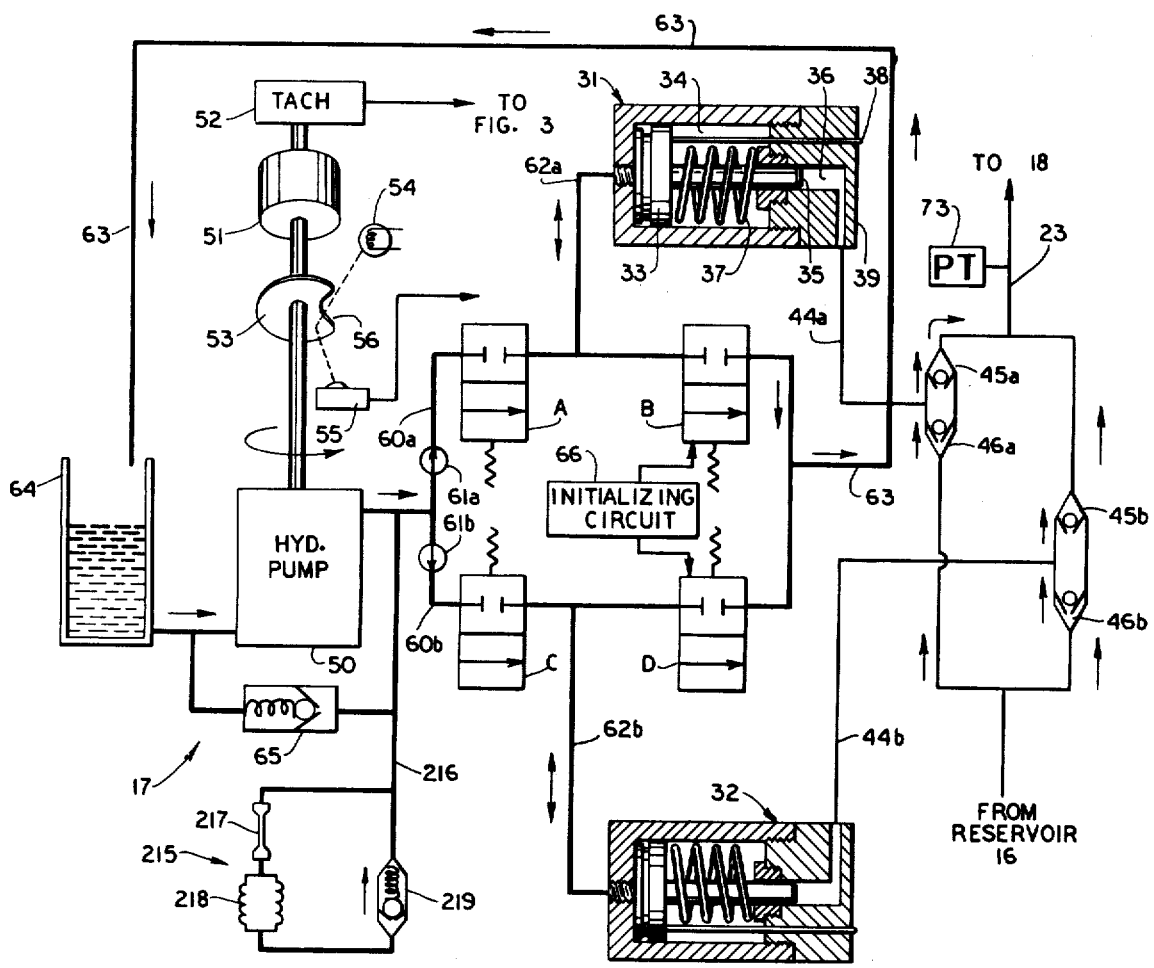
FIG. 2 shows a schematic detail view of the carrier liquid pumping system according to a disclosed embodiment of the present invention.

The pulselsss pumping system 17, as illustrated in detail in FIG. 2, includes a high-pressure output portion which supplies a substantially pulseless and continuous flow of carrier liquid, and a low-pressure input portion which utilizes controlled hydraulic pressure to operate the output portion of the pumping system. The output portion includes a first pressure intensifier 31 and a second pressure intensifier 32 which may be identical in construction to the first pressure intensifier. Each of the two pressure intensifiers, as exemplified by the first pressure intensifier 31, has an input piston 33 received for reciprocation in an input cylinder 34 and connected to impart reciprocal movement in an output piston 35 received within an output cylinder 36. The interconnected input piston 33 and output piston 35 constitute a piston assembly which is normally maintained at the position shown in FIG. 2, by a suitable biassing device such as the spring 37, whereat the liquid-receiving volume of the output cylinder 36 is maximized. The piston assembly of each pressure intensifier may be provided with an indicator member 38 which extends for reciprocal movement through an opening in the end wall 39 of the output cylinder.

The output cylinder 36 of the first pressure intensifier 31 is connected by a conduit 44a to interconnect at the junction of a first set of one-way valves 45a, 46a. In a corresponding manner, the output cylinder of the second pressure intensifier 32 is connected by the conduit 44b at the junction between a second pair of one-way valves 45b, 46b. Each of the one-way valves 45a, 45b, 46a, and 46b is of the type which permits fluid flow to occur only in the direction shown by the respective arrows positioned alongside the valve symbols, and which prevents fluid flow in the opposite direction. The inlet side of each one-way valve 46a and 46b is connected to receive carrier liquid from the reservoir 16, and the output side of each one-way valve 45a, 45b, is connected in parallel to supply pumped carrier liquid along the conduit 23 to the sample valve 18.

The low-pressure input portion of the pumping system 17 includes a source of pressurized hydraulic operating liquid such as a constant-volume hydraulic pump 50 or the like. The pump 50 can be a conventional gear pump or any other pump which operates to supply a volume of liquid at a flow rate dependent upon the input speed of the pump. Those skilled in the art will recognize that the viscosity of typical hydraulic operating liquids permits such hydraulic liquids to be readily pumped at a constant flow rate with conventional continuous-operation hydraulic pumps such as gear pumps or the like. Such conventional continuous-operation pumps are incapable of pumping the relatively low-viscosity liquids employed as chromatographic carrier liquids, at the pressures and with the degree of stable operation required for liquid chromatography.

A motor 51 is connected to drive the hydraulic pump 50 and also to drive a tachometer 52. Since the hydraulic pump 50 of the illustrative embodiment pumps a certain volume of hydraulic liquid for each rotation of the pump drive shaft, the volume of hydraulic liquid delivered by the hydraulic pump can be determined by counting shaft revolutions. The revolutions of the drive shaft are detected by suitable apparatus such as an apertured or notched disc 53 mounted on the shaft. A source of illumination 54 and an illumination sensor 55 are positioned with respect to the disc 53 so that a beam of illumination from the source 54 is allowed to strike the sensor 55 only when the aperture or notch 56 in the disc is aligned with the beam. The sensor 55 thus provides an output signal condition corresponding to each revolution of the drive shaft of the hydraulic pump 50.

The output of the hydraulic pump 50 is connected to a pair of branch lines 60a and 60b, with each such branch line including a corresponding one-way valve 61a and 61b. The branch line 60a is connected to a two-way valve A, of the type which is controllable either to be open-circuit or closed-circuit. Valve A, as well as valves B, C, and D, identified below, may be solenoid-actuated valves and are depicted in FIG. 2 in the "off" or deactivated condition in which the valve is "closed" to prevent liquid flow therethrough.

Valve A is connected to a line 62a which leads to the input cylinder 34 of the first pressure intensifier 31. The branch line 60b is connected in a corresponding manner to the normally-closed valve C, which is connected by the line 62b to the input cylinder (not designated on the drawing) of the second pressure intensifier 32.

A pressure relief valve 65 is connected between the output and the input lines of the hydraulic pump 50. The pressure relief valve 65 is adjusted to open for bypassing hydraulic liquid directly from the output to the input of the hydraulic pump 50, so as to bypass the remainder of the hydraulic circuit, when the hydraulic pressure within the circuit exceeds a predetermined amount in excess of a normal range of operating hydraulic pressure. The desirability of the pressure relief valve 50 is explained below in further detail.

The output of the hydraulic pump 50 is connected by the line 216 to a smoothing circuit 215. The smoothing circuit 215 includes a restricted-flow passage 217 connected in series with a pressure accumulator 218, and a one-way valve 219 connected to bypass the restricted-flow passage and the pressure accumulator. The one-way valve 219 permits substantially unrestricted liquid flow in the direction indicated by the arrow adjacent the one-way valve, and prevents liquid flow in the opposite direction through the valve. When the hydraulic pump 50 initially commences operation, pressurized operating liquid flows through the line 216 and through the restricted-flow passage 217 at a relatively slow rate to charge the pressure accumulator 218. Liquid flow through the restricted-flow passage 217 continues until a sufficient amount of operating liquid is received in the pressure accumulator 218 to balance the pressure in the line 216. A subsequent reduction of the operating liquid pressure in the output of the hydraulic pump 50 causes operating liquid to be expelled from the pressure accumulator 218 through the one-way valve 219 and the conduit 216, at a rate of flow which is substantially unrestricted relative to the rate of flow through the restricted-flow passage 217, so that the smoothing circuit 215 supplies pressurized operating liquid to the low-pressure input portion of the pumping system to smooth or to minimize pressure perturbations which might otherwise exceed the instantaneous liquid-delivery capacity of the hydraulic pump 50.

The hydraulic circuit as described thus far functions in a manner described below, to selectively supply hydraulic operating liquid to the pressure intensifiers 31 and 32. The return or drain circuits which allow the hydraulic operating liquid to flow away from the pressure intensifiers include the valves B and D, along with the return line 63 extending to the reservoir 64 which is connected to the liquid input of the hydraulic pump 50. The valves B and D are operationally connected to an initializing circuit 66 for a purpose described below.

It will now be appreciated that hydraulic fluid flows from the hydraulic pump 50 to the input cylinder of the first pressure intensifier 31 when the valve A is opened. Any carrier liquid which is present in the output cylinder 36 of the first pressure intensifier is displaced by the output piston 35 and flows through the conduit 44a and the one-way valve 45a to enter the conduit 23. The second pressure intensifier 32 is similarly operated upon the opening of the valve C to force carrier liquid along the conduit 44b and through the one-way valve 45b to enter the conduit 23. The piston assembly in either of the pressure intensifiers continues to travel in the right-hand direction (as viewed in FIG. 2) either until the piston assembly reaches the end of stroke, or until the corresponding supply valve A or C is closed. Thereafter, the hydraulic liquid is drained from the respective input cylinders by selective opening of valves B and D, respectively, so that the piston assembly moves leftward under the influence of the spring 37 to displace the hydraulic operating liquid out of the input cylinder and through the return line 63 to the reservoir 64. The foregoing pumping and return operations of the pressure intensifiers occur in a particular sequence of operational steps, as explained hereinbelow.

As the piston assembly of the first pressure intensifier 31 is moved leftward by the spring 37, a fresh supply of carrier liquid from the reservoir 16 is drawn through the one-way valve 46a to enter the output cylinder 36. The output cylinder of the second pressure intensifier 32 is similarly recharged with carrier liquid through the one-way valve 46b.

Figure 3:
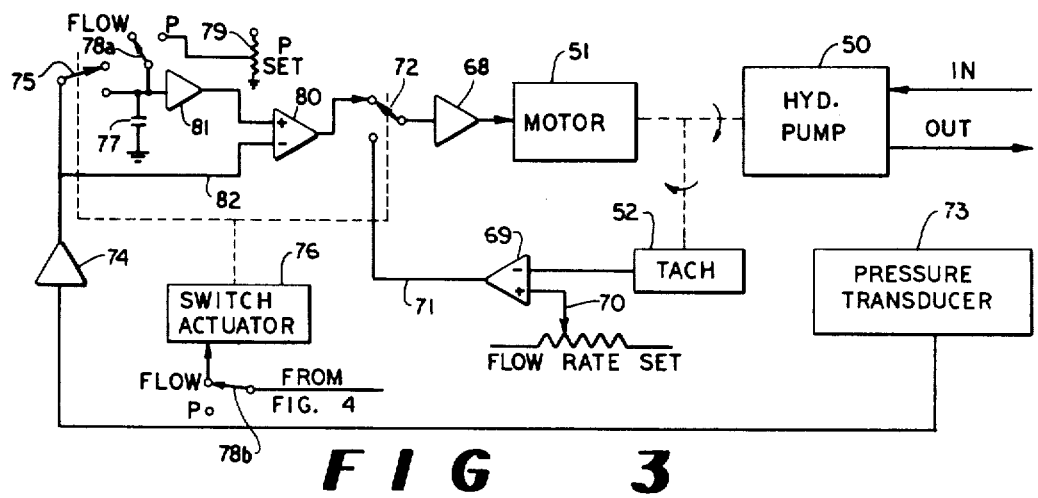
FIG. 3 shows a schematic view of a circuit for controlling the operation of the pumping system shown in FIG. 2.

During the operation of the carrier liquid pumping system of the present invention, as described in detail below, carrier liquid is delivered at a constant rate of flow during one portion of each complete operating cycle, and is delivered at a constant pressure during another portion of the operating cycle. The hydraulic pump 50 is selectively operated to provide either constant-rate or constant-pressure flow of the carrier liquid in accordance with a control circuit as shown in FIG. 3. Operating power is supplied to the pump driving motor 51 through a power amplifier 68, and the tachometer 52 is driven by the hydraulic pump drive shaft to provide an output signal which is a function of the drive motor-hydraulic pump rotational speed. The tachometer output signal is supplied as an input signal to the differential amplifier 69. The differential amplifier 69 also receives an input signal 70 which is selectively adjustable to correspond to a desired preset constant flow rate of carrier liquid. The output signal from the differential amplifier 69 is connected by the line 71 to one contact of the switch 72. The constant-pressure/constant-rate selector switches 78a and 78b are assumed to be in the "flow" position, as depicted in FIG. 3, to select constant flow rate operation.

The pressure of the carrier liquid being pumped into the line 23 is measured by a pressure transducer 73, and the pressure-related output signal of the transducer 73 is amplified at 74 and supplied to the switch 75. The switches 72 and 75 are ganged together for concurrent actuation by the switch actuator 76. When both of the switches 72 and 75 are operated by the actuator 76 to the lower contact position (opposite to the position depicted in FIG. 3), the amplified signal from the pressure transducer 73 is applied to charge a capacitance 77. At the same time, the output signal from the differential amplifier 69 is applied along the line 71 and through the switch 72 to provide an input control signal to the power amplifier 68.

With the switches 72 and 75 in the aforementioned lower position, accordingly, the hydraulic pump motor 51 is operating in a feedback control circuit which maintains the rotational speed of the hydraulic pump 50 at a constant speed which is determined by the set input signal 70 to the differential amplifier 69. Since the hydraulic pump 50 pumps hydraulic operating liquid at a rate of flow determined by the rotational input speed, it will be understood that the constant flow of hydraulic fluid is applied to only one of the pressure intensifiers 31 and 32, and that the feedback-maintained constant-speed drive of the hydraulic pump provides a constant-rate flow of hydraulic operating liquid which can be supplied to either one of the pressure intensifiers 31 and 32 to pump carrier liquid through the conduit 23 at some constant flow rate which is dependent upon the preset speed of the motor 51. The pressure developed in the conduit 23 during constant-rate of flow of the carrier liquid is measured by the pressure transducer 73, and the resultant amplified pressure signal is applied to charge the capacitance 77 to a charge level which is dependent upon the measured pressure in the conduit 23.

When the switches 72 and 75 are operated by the actuator 76 to assume the upper switch position, depicted in FIG. 3, the input signal to the power amplifier 68 is switched from the tachometer-related signal on the line 71 and is connected to the output of the differential amplifier 80. One input to the differential amplifier 80 is received from the capacitance 77 by way of the buffer amplifier 81, while another input of the differential amplifier 80 is connected to receive the amplified signal from the pressure transducer 73.

With the switches 72 and 75 in the aforementioned upper position, the power amplifier 68 receives an operating control signal which is a function of the pressure-related charge previously applied to the capacitance 77 during constant-flow operation of the pumping system, and the motor 51 is thus controlled to drive the hydraulic pump 50 to deliver a flow of hydraulic fluid sufficient to maintain the carrier liquid pressure in the conduit 23 at the pressure previously measured during constant-volume operation. At the same time, the pressure signal from the transducer 73 is applied along the line 82 to the differential amplifier 80 to provide a pressure-related feedback signal to the differential amplifier, thereby causing the power amplifier 68 to operate the motor 51 as required to maintain the carrier liquid pressure at the pressure previously developed during constant-flow operation of the pumping system.

It will be understood that the buffer amplifier 81 has sufficiently high input impedance so as not to materially discharge the capacitance 77 during the desired time span of constant-pressure operation, as set forth below. In an actual embodiment of apparatus according to the present invention, a buffer amplifier 81 has been used which will hold a charge of the capacitance 77 to within one percent over a period of four minutes, although the present invention is not intended to be limited by the aforementioned time or tolerance.

Continuous operation of the present carrier liquid pumping system at a selected constant pressure is obtained by moving the selector switches 78a and 78b to the "P" position (opposite the respective positions depicted in FIG. 3), whereupon the switch actuator 76 is disabled and the switches 72 and 75 remain in the depicted upper contact positions. The amplifier 80 now receives one input signal from the pressure-set potentiometer 79, corresponding to a desired carrier liquid pressure, and receives another input on the line 82 corresponding to the carrier liquid pressure measured by the pressure transducer 78. The amplifier 80 provides an output signal to operate the motor 51 as required to maintain the carrier liquid pressure at the pressure selected by adjustment of the potentiometer 79. In the constant-pressure mode of operation, the carrier liquid pressure is held steady and the flowrate is allowed to vary as the permeability of the chromatograph column changes.

Figure 4:
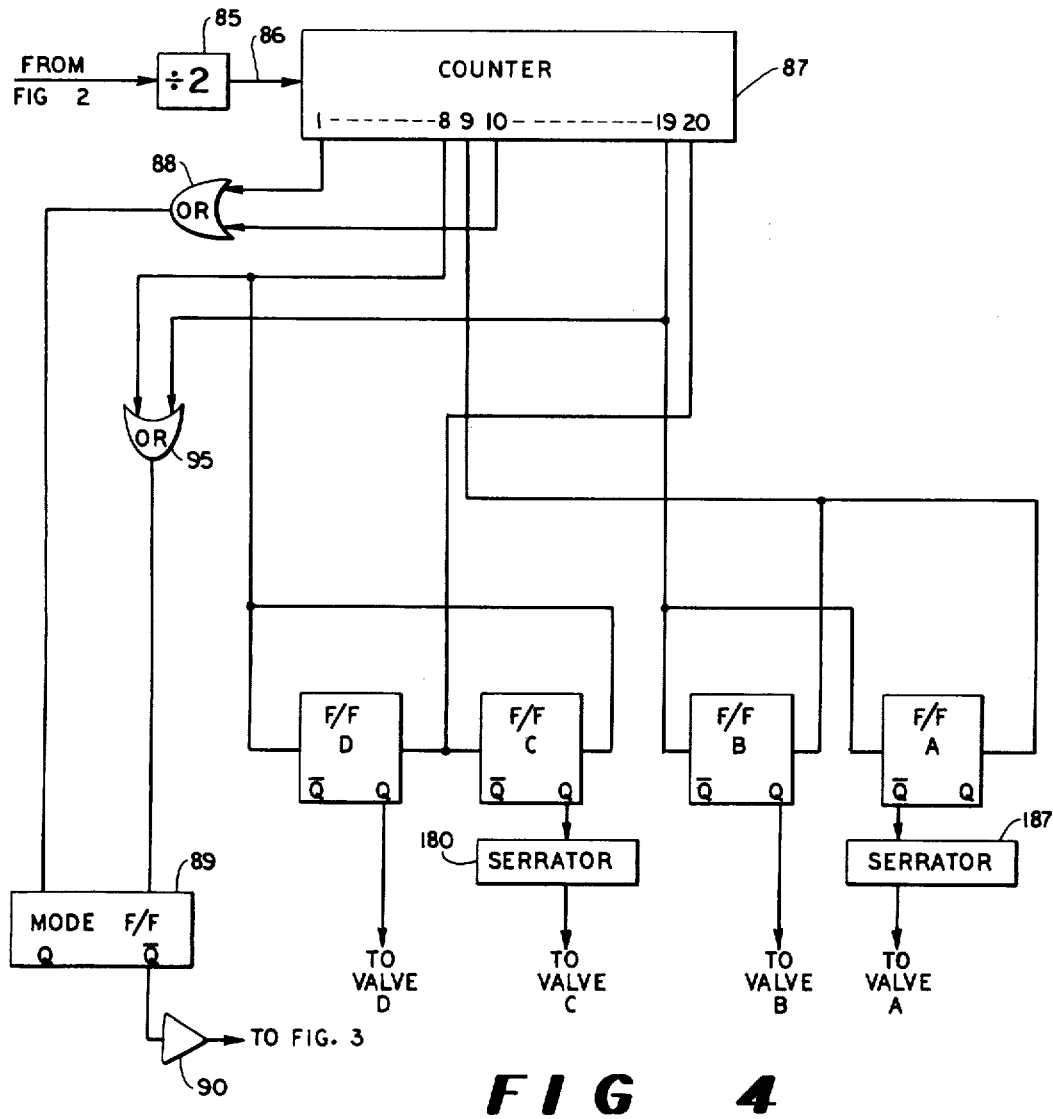
FIG. 4 shows a schematic diagram of a sequence control circuit included in the illustrative embodiment of the present pumping system.

The operation sequence of the carrier liquid pumping system of the present invention is provided in the disclosed embodiment by selective control of the hydraulic fluid valves A–D and by the interrelated selective control of the pumping system in the aforementioned constant-rate of flow and constant-pressure modes of operation. The operational control is provided with the sequence control apparatus depicted in FIG. 4, in the disclosed illustrative embodiment of the present invention. It will be apparent to those skilled in the art, however, that the particular arrangement of apparatus shown in FIG. 4 is determined by the specific operational sequence of the disclosed embodiment; variations in the aforementioned disclosed sequence of operation may be made within the scope of the present invention; however, and such variations may require corresponding changes in the sequence control system. The sequence control system shown in FIG. 4 provides a programmed sequence of operational steps, with the programmed sequence being keyed to the drive shaft rotation of the constant-volume hydraulic pump 50. The sequence control circuit of FIG. 4 may, accordingly, be considered as a special-purpose logic control circuit. It is considered to be well within the abilities of a skilled computer programmer, however, to instruct an appropriate general-purpose digital computer to provide the same or a similar sequence of operational control function signals for the hydraulic system.

The control signals provided by the sensor 55 in response to each rotation of the drive shaft of the hydraulic pump 50 are supplied to a divider circuit 85, which functions to provide an output pulse on the line 86 for every other input pulse provided by the sensor 55. The output pulses from the divider circuit 85 are supplied as a clock pulse input to the twenty-place counter 87. The counter 87 has twenty output states (in the disclosed illustrative embodiment) and sequentially steps an output logic signal condition in ascending order of output circuits, in response to each pulse applied along the line 86 to the clock pulse input. When the counter 87 has been counted to position "twenty", the next clock input pulse resets the counter to the "one" state. Those skilled in the art will recognize that a twenty-position counter may in practice be provided by an appropriate combination of a ten-position counter and a flip-flop circuit connected to function as a times-two circuit.

Additional details of the sequence control system are discussed along with the following operational description of the carrier liquid pumping system as described thus far. It is assumed for the purpose of explanation that the counter 87 has just been reset to the "one" position by a clock pulse and is being progressively counted upwardly by clock pulses generated in response to every other revolution of the input shaft to the hydraulic pump 50. Referring to the control sequence diagram shown in FIG. 5, it will be seen that the hydraulic supply valve A is open and the hydraulic supply valve B is closed, so that the entire hydraulic fluid output of the hydraulic pump 50 is being supplied to operate the first pressure intensifier 31. The "one" output from the counter 87 is applied through the "OR" gate 88 to place the $\bar{Q}$ output of the mode flip-flop 89 in a low state, and this output is inverted at 90 and supplied as an input to the switch actuator (FIG. 3). The switches 72 and 75 are operated by the switch actuator 76 to assume the constant-rate of flow mode of pumping operation, and so the first pressure intensifier 31 presently receives hydraulic fluid pumped at a constant flow rate to provide a constant-rate of flow of carrier liquid, the exact flow rate of the carrier liquid being determined by adjustment of the set input 70.

This operation of the first pressure intensifier 71 continues until the piston assembly of the first pressure intensifier nearly reaches the maximum extent of travel. Since the hydraulic pump 50 pumps a certain fixed volume of hydraulic liquid in response to each revolution of the pump input shaft, and since the effective volume of the input cylinder 34 can be readily determined, the number of input shaft revolutions necessary to provide any predetermined amount of travel of the pressure intensifier piston assembly can be readily determined. The hydraulic supply valve A in the disclosed embodiment is closed after seventeen revolutions of the pump input shaft, corresponding to the trailing edge of logic count "nine" applied to flip-flop A of the sequence control apparatus.

Although it might seem desirable to open the hydraulic valve C simultaneously with the closure of the supply valve A so that the second pressure intensifier 32 could commence delivering carrier liquid simultaneously with the termination of the first pressure intensifier 31, unwanted pressure pulsations and fluctuations in the carrier liquid supply are caused by such a changeover. Among the factors contributing to such pressure fluctuations are the expansion of the tubing comprising the various hydraulic lines and carrier liquid lines, irregularities of volume due to expansion of liquid seals in the low-pressure and high-pressure portions of the system, and the slight but nonetheless material effect of liquid expansion. The one-way valves 45a, 45b, 46a, and 46b, are another source of unwanted volumetric change; although one-way valves are normally considered to allow liquid flow in only one direction, the initiation of pressure on the conduit 44b (for example) causes the ball (or other movable element) of the one-way valve 46b to undergo some slight amount of movement while becoming firmly seated in flow-blocking position. This initial seating movement of the one-way valves slightly changes the overall volume of the carrier liquid conduit system, and the volumetric change produces a corresponding fluctuation in the pressure within that system.

These and other flow-rate irregularities are eliminated or greatly attenuated by pre-pressurizing the second pressure intensifier before completing the transition from the first pressure intensifier to the second pressure intensifier. Referring again to FIG. 5, it is seen that the hydraulic supply valve C is opened at the eighth clock pulse as flip-flop C is shifted to the Q output in response to the trailing edge of clock pulse "eight". For a period of two revolutions of the hydraulic pump input shaft, accordingly, hydraulic supply valves A and C are both open to supply hydraulic liquid to both of the pressure intensifiers 31 and 32. The Q output signal from the flip-flop C passes through a serrator 180 which "serrates" or repetitively interrupts, for an initial period of time, the operating signal applied to open the valve C. These serrations of the operating signal, which are indicated at 91 on FIG. 5 and which may consist of approximately four signal interruptions per second over a period of about four seconds, allow hydraulic liquid to be supplied to the second pressure intensifier 32 in varying increments which initially pressurize the input cylinder of that intensifier while avoiding the drop in hydraulic pressure which would result if the empty and unpressurized input cylinder of the second pressure intensifier were simply dumped onto the hydraulic system in parallel with the input cylinder of the first pressure intensifier 31.

Figure 12:
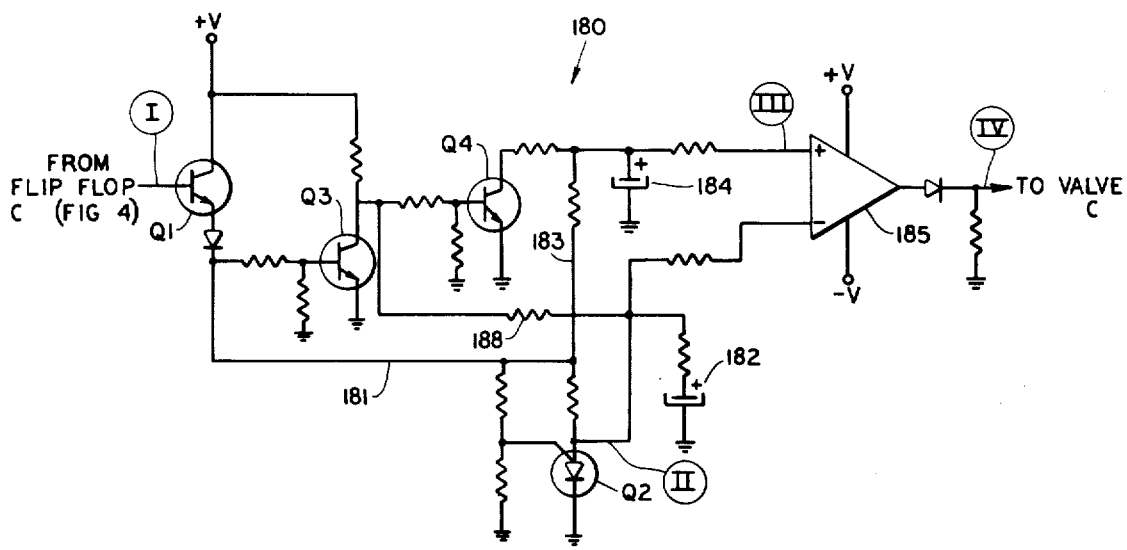
FIG. 12 is a schematic diagram showing a waveform serrator according to a disclosed embodiment of the present invention.

An illustrative embodiment of the serrator 180 is shown in FIG. 12, where the operating signal from the flip-flop C is applied to the base of the transistor Q1 which is connected to operate as an emitter-follower. The operating signal turns on transistor Q1 to apply voltage along the line 181 to operate a sawtooth relaxation oscillator including the transistor Q2 and the capacitance 182. The conductive state of transistor Q1, in response to a valve operating signal, also applies voltage along the lines 181 and 183 to commence charging the capacitance 184. The positive input of the differential amplifier 185 is connected to the capacitance 184, and the negative input of the differential amplifier is connected to receive the output of the aforementioned sawtooth oscillator. The transistor Q3 is turned on when the transistor Q1 conducts, and turning-on of Q3 causes the previously-conducting transistor Q4 to become turned off.

Figure 13:
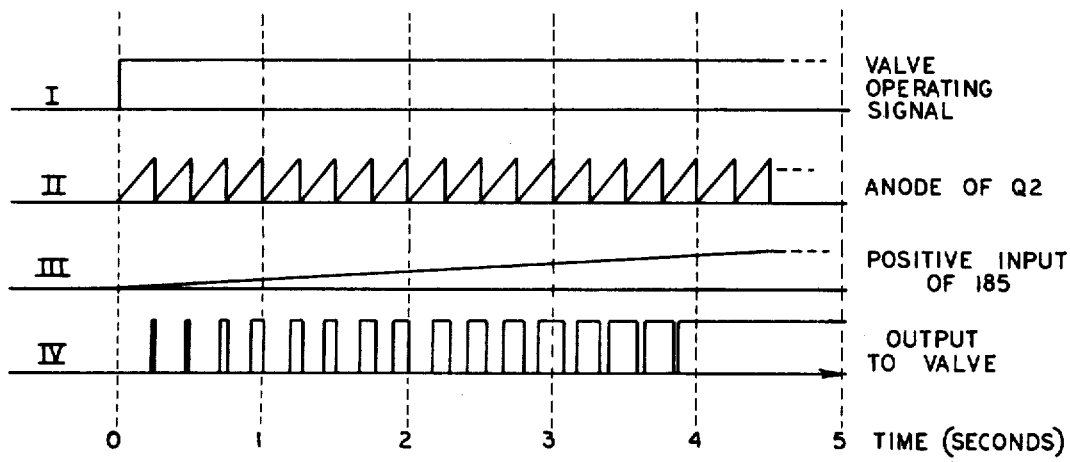
FIG. 13 shows several waveforms which occur in operation of the circuit shown in FIG. 12.

The operation of the serrator 180 is best understood with reference to the serrator waveforms shown in FIG. 13. Q1 and Q3 are turned off in the absence of a valve operating signal, allowing Q4 to turn on and discharge capacitance 184 to zero volts. The negative input of the differential amplifier thus receives a small positive bias voltage applied through the resistance 188, insuring that the output of the differential amplifier will be low whenever the input to Q1 is low. Application of the operating signal from the flip-flop C is shown in waveform I of FIG. 13, and consists of a rectangular waveform constituting the Q output signal of that flip-flop. The transistor Q1 of the serrator becomes conductive in response to the operating signal input, and the sawtooth generator immediately commences operating to provide the sawtooth waveform of FIG. 13(II) at the anode of Q2. This sawtooth waveform is applied to the negative input of the operational amplifier 185. The capacitance 184 commences accumulating a charge at the same time that the sawtooth oscillator commences operation, since Q4 is now turned off and it will be apparent from waveforms II and III of FIG. 13 that the time constant of the charge circuit for the capacitance 184 is considerably longer than the time constant for charging the capacitance 182 of the sawtooth oscillator. The differential amplifier 185 provides a positive output only when the amplifier positive input (which receives the ramp signal provided by the relatively slow-charging capacitance 184,) exceeds the amplitude of the sawtooth signal applied to the amplifier negative input. The amplifier 185 thus functions as a voltage comparator and commences providing a positive output signal as soon as an individual sawtooth waveform falls to zero, and continues providing such positive output until the amplitude of the next sawtooth cycle rises to the voltage of the ramp signal.

The positive output of the operational amplifier 185, as shown in waveform IV of FIG. 13, thus consists of a series of pulses, with the duration of each pulse being greater than the duration of the immediately-preceding pulse. At a time determined by the parameters of the serrator circuit, the ramp voltage exceeds the maximum sawtooth voltage and the differential amplifier 185 provides an uninterrupted output signal 186 thereafter. Since the valve C is momentarily opened in response to each of the pulses shown in the waveform IV, it can be seen that the serrator initially operates to pulse the valve C open for a number of intervals of increasing duration, after which the valve C remains continuously open until the operating signal from the flip-flop C terminates. The transistor Q1 thereupon becomes nonconductive, turning off the transistor Q3 and allowing the transistor Q4 to become conductive. The capacitance 184 is discharged through transistor Q4, whereupon the positive output of the operational amplifier 185 terminates.

The specific number of the serrations or operating pulses shown in the waveform IV is not critical, so long as initial precharging of the second pressure intensifier is accomplished within the capability of the hydraulic system to compensate for the corresponding added volume of fluid to be pumped. The duration of the individual operating pulses is shortest at the beginning of each valve opening cycle, so that the empty input cylinder of the pressure intensifier initially receives commensurately small increments of hydraulic liquid.

The disclosed embodiments of the present invention include other features further minimizing the pressure perturbations which might otherwise occur when a valve A or C is initially opened to connect the empty and unpressurized input cylinder of a pressure intensifier to receive operating liquid. The two one-way valves 61a and 61b in the branch lines extending to the valves A and B, respectively, prevent operating liquid from flowing out of a pressurized pressure intensifier and into the unpressurized input cylinder of another pressure intensifier, during the times when both valve A and C are concurrently open.

The smoothing circuit 215 stands ready to return pressurized operating liquid from the pressure accumulator 218 into the hydraulic circuit through the one-way valve 219, in response to a momentary drop in hydraulic system pressure occasioned, for example, by connection of an unpressurized pressure intensifier to the hydraulic system. The smoothing circuit 215 thus operates to supplement the flow of hydraulic liquid in the hydraulic circuit, in response to a transient demand condition which might otherwise exceed the volumetric supply capability of the hydraulic pump 50. After the transient demand condition terminates, the pressure accumulator 218 is recharged through the restricted-flow passage 217 at a slow rate, relative to the rate of operating liquid discharge through the one-way valve 219, so that recharging of the pressure accumulator occurs at a rate which does not overload the volumetric capacity of the hydraulic pump 50.

The hydraulic pumping system is switched from the constant-flow operating mode to the constant-pressure operating mode, before the input cylinders of the two pressure intensifiers are connected in parallel. This is accomplished in response to the leading edge of the eighth clock pulse, supplied through the OR gate 96 to shift the mode flip-flop 89 to a high $\bar{Q}$ output, whereupon the switch actuator 76 operates the switches 72 and 75 to select the constant-pressure mode of pump operation. The circuitry including the capacitance 77 functions as a memory circuit to remember the carrier liquid pressure measured during the preceding constant-flow operation, and the hydraulic pump 50 supplies hydraulic operating liquid to operate the first pressure intensifier 31 at a rate which maintains the carrier liquid pressure stored in memory. When the valve C is subsequently opened (at the trailing edge of the eighth shift pulse) to connect the second pressure intensifier 32 in parallel with the first pressure intensifier 31, the volumetric output of the hydraulic pump 50 is automatically adjusted by the constant-pressure feedback control circuit to supply the additional volume of hydraulic liquid necessary to supply hydraulic operating liquid to both pressure intensifiers while maintaining the carrier liquid pressure at the previously measured level stored in memory. During the time that both of the valves A and C are open and the two pressure intensifiers 31 and 32 are thus connected in parallel, it will be understood that the hydraulic operating liquid applied to the input cylinder of the second pressure intensifier 32 may commence operating that pressure intensifier to deliver carrier liquid through the conduit 44b concurrent with delivery of carrier liquid through the conduit 44a by the first pressure intensifier 31. The volume of hydraulic liquid applied to the two parallel pressure intensifiers by the hydraulic pump 50 is automatically adjusted by the constant-pressure feedback circuit to maintain the previously remembered pressure in the conduit 23, however, irrespective of the particular division of operation between pressure intensifiers and also irrespective of volumetric variables such as expansion of tubing, seating of one-way valves, and the like.

Figure 5:
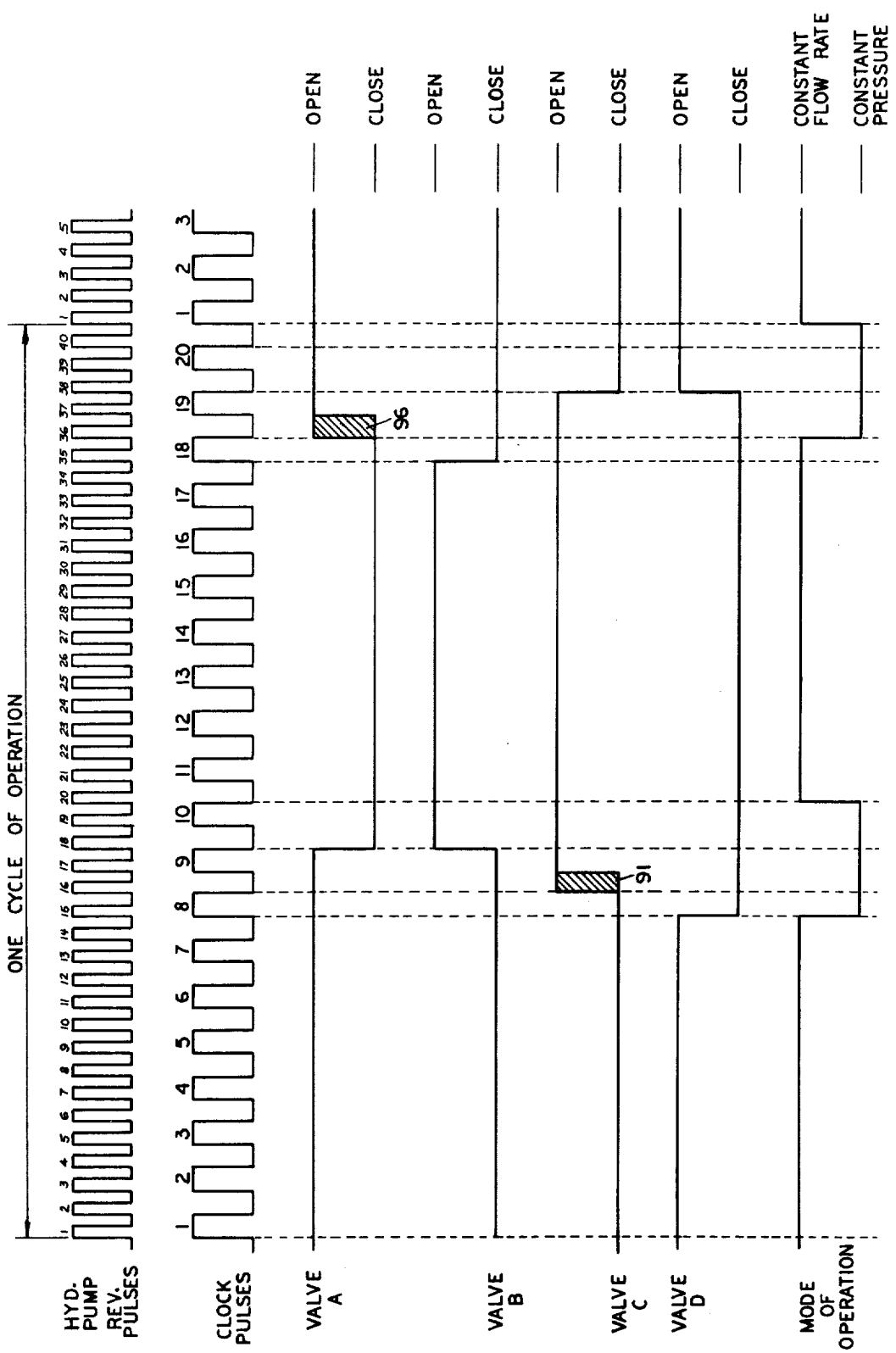
FIG. 5 is a graphical representation depicting operation of the pump system shown in FIGS. 2–4.

The two pressure intensifiers 31 and 32 are thus operated in parallel for the time required to pre-pressurize the second pressure intensifier to the pressure previously measured during constant-flow operation. After sufficient time has elapsed for satisfactory pre-pressurization, the valve A is closed and the sequence control system thereafter reverts to constant-flow operation of the second pressure intensifier 32 only. It is seen in FIG. 5 that valve A is closed at the trailing edge of clock pulse "nine", as applied to flip-flop A, and the constant-flow mode of operation is selected in response to the trailing edge of clock pulse "ten" as applied through the OR gate 88 to the mode flip-flop 89. Concurrent with the closing of valve A, hydraulic drain valve B is opened in response to clock pulse "nine" applied to flip-flop B, and the spring 37 in the first pressure intensifier 31 returns the piston assembly to the position shown in FIG. 2 to draw an additional quantity of carrier liquid into the output cylinder 36. The drain valve B remains open until the leading edge of clock pulse "eighteen", immediately preceding the opening of valve A for the next cycle of operation.

It is also apparent from FIG. 5 that a similar transition occurs from the second pressure intensifier to the first pressure intensifier occurs commencing at clock pulse "eighteen" whereat the control mode again changes from constant-flow to constant-pressure operation and the valve A is opened. The operating signal of the valve A is applied to a serrator 187, which may be identical in design and operation to the serrator 180, and the opening of the valve is serrated as shown at 96 in FIG. 5. The first pressure intensifier 31 is thus pre-pressurized and the second pressure intensifier 32 is subsequently (at clock pulse "nineteen") closed; the transition from the second pressure intensifier 32 back to the first pressure intensifier 31 is completed by the return of operational control to the constant-flow mode at the leading edge of the next clock pulse "one". The first pressure intensifier 31 is again supplying carrier liquid in the constant-flow mode, and so one complete cycle of operation of the carrier liquid pumping system has been completed.

It will be apparent that the foregoing operating cycle of the carrier liquid pumping system can be repeated indefinitely so long as a supply of carrier liquid is maintained in the reservoir 16. Since the liquid supply in the reservoir 16 can be replenished as desired, chromatographic analyses of indefinite duration can be accomplished with the present invention without pump-imposed limitations on the available amount of carrier liquid.

If the carrier liquid pumping system is turned off at a time when one of the pressure intensifiers has partially completed an operating stroke, hydraulic liquid is retained in the input cylinder of that pressure intensifier. Since the sequence counter 87 becomes reset to zero when the system is turned off, it is possible that the first operational cycle of subsequent system operation may call for a full cycle of hydraulic liquid to be supplied to that pressure intensifier which remains partially filled with hydraulic liquid. To prevent overloading and possible damage to the hydraulic system, the initializing circuit 66 is connected to open each of the return valves B and D, independently of the sequence control system shown in FIG. 4, for a period of time which is sufficient to allow all of the pressure intensifiers to be returned to the initial position depicted in FIG. 2. The initializing circuit can be connected in any appropriate manner to function in response to operation of a main switch (not shown) for the chromatograph system.

Further protection against overloading of the hydraulic system is provided by the pressure relief valve 65, which opens to limit the maximum hydraulic pressure resulting from failure of the initializing circuit or from any other malfunction which would otherwise produce excessive hydraulic pressure.

Those skilled in the art will also realize that the single hydraulic pump 50 which supplies hydraulic operating liquid to each pressure intensifier could be replaced, if desired, by a separate hydraulic pump and associated plumbing for selectively supplying hydraulic operating liquid to each pressure intensifier.

An actual embodiment of a carrier liquid pumping system as described above utilizes a pair of pressure intensifiers each having an output cylinder volumetric capacity of 2.5 cc of carrier liquid. With an operating cycle based on 40 revolutions of the hydraulic pump drive shaft, it can be seen that the volume of each pressure intensifier input cylinder and the volumetric output-per-revolution of hydraulic operating liquid from the hydraulic pump 50 are selected to provide substantially a complete stroke of pressure intensifier operation in response to 40 revolutions of the hydraulic pump drive shaft. It will be understood that the selection of 40 shaft revolutions (as well as the selection of 20 shift pulses) to define one cycle of operation is by way of example only, and that either a greater or lesser number of shaft revolutions and/or shift pulses can be selected to define a complete cycle of operation.

Figure 6:
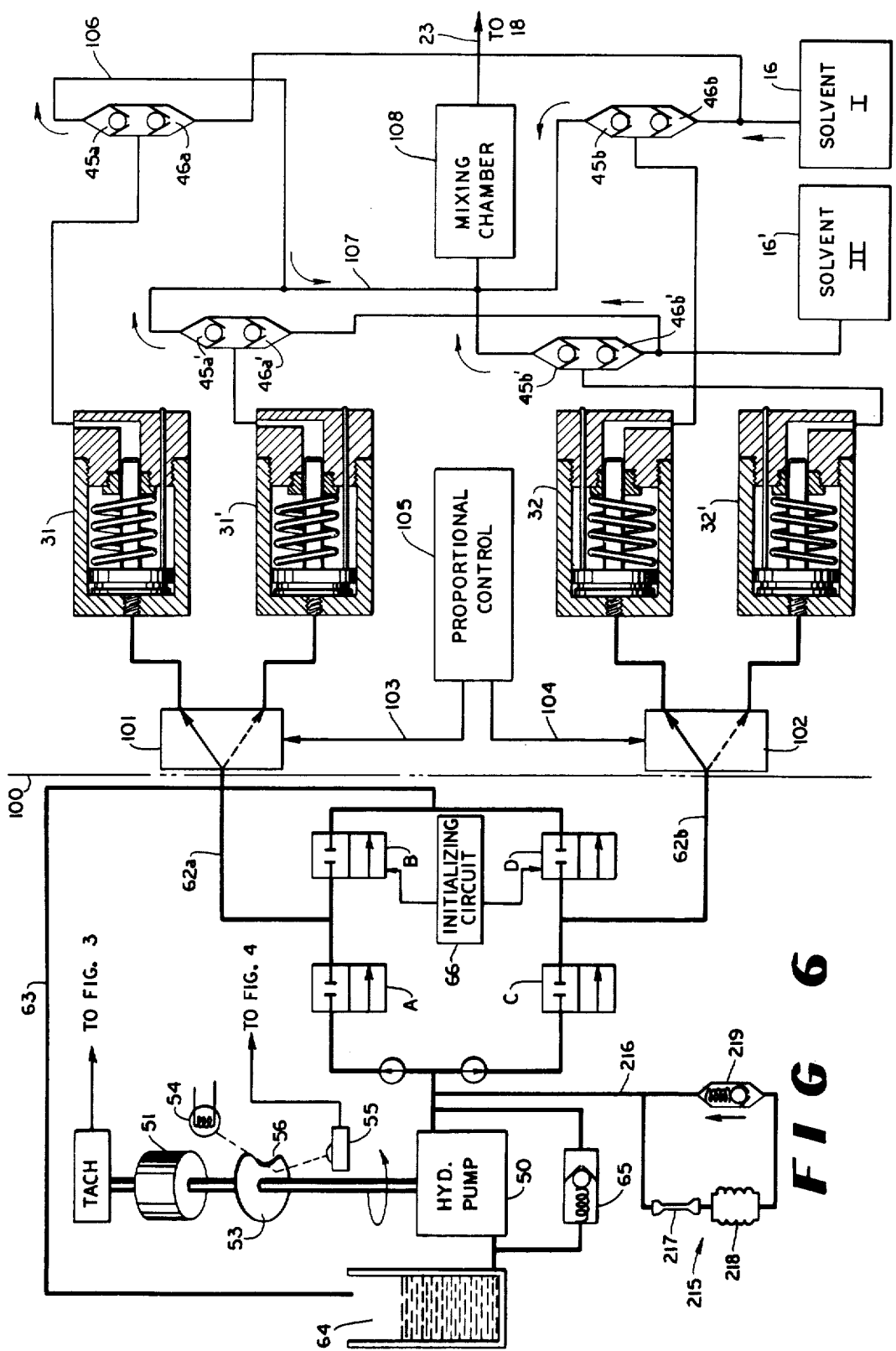
FIG. 6 is a block diagram of a carrier liquid pumping system according to another illustrative embodiment of the present invention, used for pumping two different carrier liquids.

It is frequently desirable to use more than one carrier liquid during an operating run of a liquid chromatograph. For example, it may be desirable to selectively change from a first carrier liquid (such as a polar solvent) to a second carrier liquid (such as a nonpolar solvent) in a preprogrammed manner in the course of chromatographic analyses. A modification of the present liquid chromatograph to permit preprogrammed use of two different carrier liquids is shown in FIG. 6, wherein like reference numerals are used to denote like elements as shown in FIG. 2 and wherein primed reference numerals are used to denote elements which duplicate corresponding elements shown in FIG. 2. Generally, the elements to the left of the dividing line 100 in FIG. 6 are included in the pumping system embodiment depicted and previously described with respect to FIG. 2, and the hydraulic liquid supply valves A, C, and the drain valves B and D are operated in the same manner and sequence as previously described with respect to FIGS. 2–5.

With reference to FIG. 6, the pressure intensifiers 31' and 32' are provided in addition to the first and second pressure intensifiers 31 and 32 as previously described. All four of the pressure intensifiers are preferably operationally identical. The output cylinder of the additional pressure intensifier 31' is connected through a one-way valve arrangement 45a' and 46a', while the output cylinder of the additional pressure intensifier 32' is connected to the arrangement of one-way valves 45b' and 46b'. The inlet sides of the one-way valves 46a' and 46b' are connected to a second carrier liquid reservoir 16'. The second reservoir 16' may for convenience be identified as containing "solvent II". The one-way valves associated with the pressure intensifiers 31 and 32 are connected as before to the reservoir 16, designated in FIG. 6 as containing "solvent I".

The hydraulic line 62a extends from the junction of valves A and B to the inlet side of a distribution valve 101, which is selectively operable to connect the line 62a to the input cylinders of either pressure intensifier 31 or 31'. The hydraulic line 62b is correspondingly connected to the input side of another distribution valve 102, which is selectively operable to connect the line 62b to the input cylinders of either pressure intensifier 32 and 32'. Each of the distribution valves 101 and 102 may be a solenoid-actuated two-way valve which provides a first flow connection when deenergized and which provides a second flow connection when energized. The distribution valves 101 and 102 are operated in response to control signals provided along respective control lines 103 and 104 from the proportional control apparatus 105. The proportional apparatus 105 may be provided by any appropriate circuit arrangement which supplies operating power to the distribution valves 101 and 102 proportional to the desired relative proportions of solvent I and solvent II. Sequencing circuits and devices to accomplish the foregoing proportional control are within the ability of those skilled in the art, and are not disclosed in further detail herein.

Considering the operation of the embodiment depicted in FIG. 6, it is first assumed that only solvent I is desired for use in a chromatograph operation. The proportional control apparatus 105 is actuated to control the distribution valves 101 and 102 to maintain the pressure intensifiers 31 and 32 in constant communication with the respective hydraulic lines 62a and 62b. It will be understood that these flow positions of the distribution valves 101 and 102 may be the normal deenergized positions of such valves. It will also be seen that the two pressure intensifiers 31 and 32 function to pump solvent I from the reservoir 16, through the one-way valves 45a, 46a, the carrier liquid conduits 106 and 107, the mixing chamber 108, and thence by way of the conduit 23 either to the sample introduction valve 18 or directly to the chromatograph column.

If it is desired to supply the chromatograph column with a mixture of solvents I and II, the distribution valves 101 and 102 are actuated by the proportional control 105 to supply hydraulic liquid to the pressure intensifiers 31' and 32'. The pressure intensifiers 31' and 32' must receive hydraulic liquid for a proportionate part of each pump operating cycle (as defined in FIG. 5) which is equal to the desired proportion of solvent II. For example, a carrier liquid mixture consisting of 90% solvent I and 10% solvent II is provided by operating the distribution valves 101 and 102 to supply hydraulic liquid to the pressure intensifiers 31' and 32' during 10% of each operating cycle. Since the combined flow of carrier liquid delivered to the chromatograph column should be an intermixture of solvents I and II, and not merely alternate segments of unmixed solvent, it is preferred to pulse the distribution valves 101 and 102 at some predetermined rate during each complete operating cycle of the pumping system. By way of example, the distribution valves can be supplied with operating signals from the proportional control 105 at a rate of one pulse per second, it being understood that the relative duration of "on-time" for each such complete pulse must be chosen to provide the corresponding duration of operating time for the pressure intensifiers 31' and 32' which is necessary to provide the desired proportion of solvent II.

If a 50–50 ratio of solvents I and II are desired, for example, it will be understood that the "on-time" of each such pulse is exactly equal to the "off-time" of each complete pulse. If each of the four pressure intensifiers has an output cylinder capacity of 2.5 ml and a carrier liquid flow rate of 1 ml per minute into the chromatograph column is desired, 2.5 minutes are required for each half-cycle of operation. The distribution valves 101 and 102 are pulsed at the rate of 60×2.5, or 150 pulses for each such half-cycle of operation. A complete operating cycle of the pump system will require 300 pulses of the distribution valves, using the selected illustrative data. During each illustrative complete operating cycle of the pumping system, the mixing chamber 108 receives 150 segments of solvent I and 150 segments of solvent II, although the relative amounts of the solvent segments are determined by the desired programmed time-proportion of solvents I and II.

If it is desired to transfer from solvent I to solvent II in some predetermined manner of transfer, such as a linear or nonlinear progression from solvent I to solvent II over a predetermined time period, the proportional control 105 is simply actuated to vary the proportion of "on-time" control of the distribution valves 101, 102 in accordance with the desired progression of transfer. Since the transfer between solvents is controlled by the operation of the distribution valves 101 and 102, rather than by any fixed mechanical drive linkage, this transfer need not be linear with respect to time and can instead be along a transfer slope having any desired curvature which can be programmed into the proportional control 105. Carrier solvent transfer can thus be readily accomplished along time-based slopes having various convex or concave curvatures at the desire of the operator.

Figures 6A, 14:
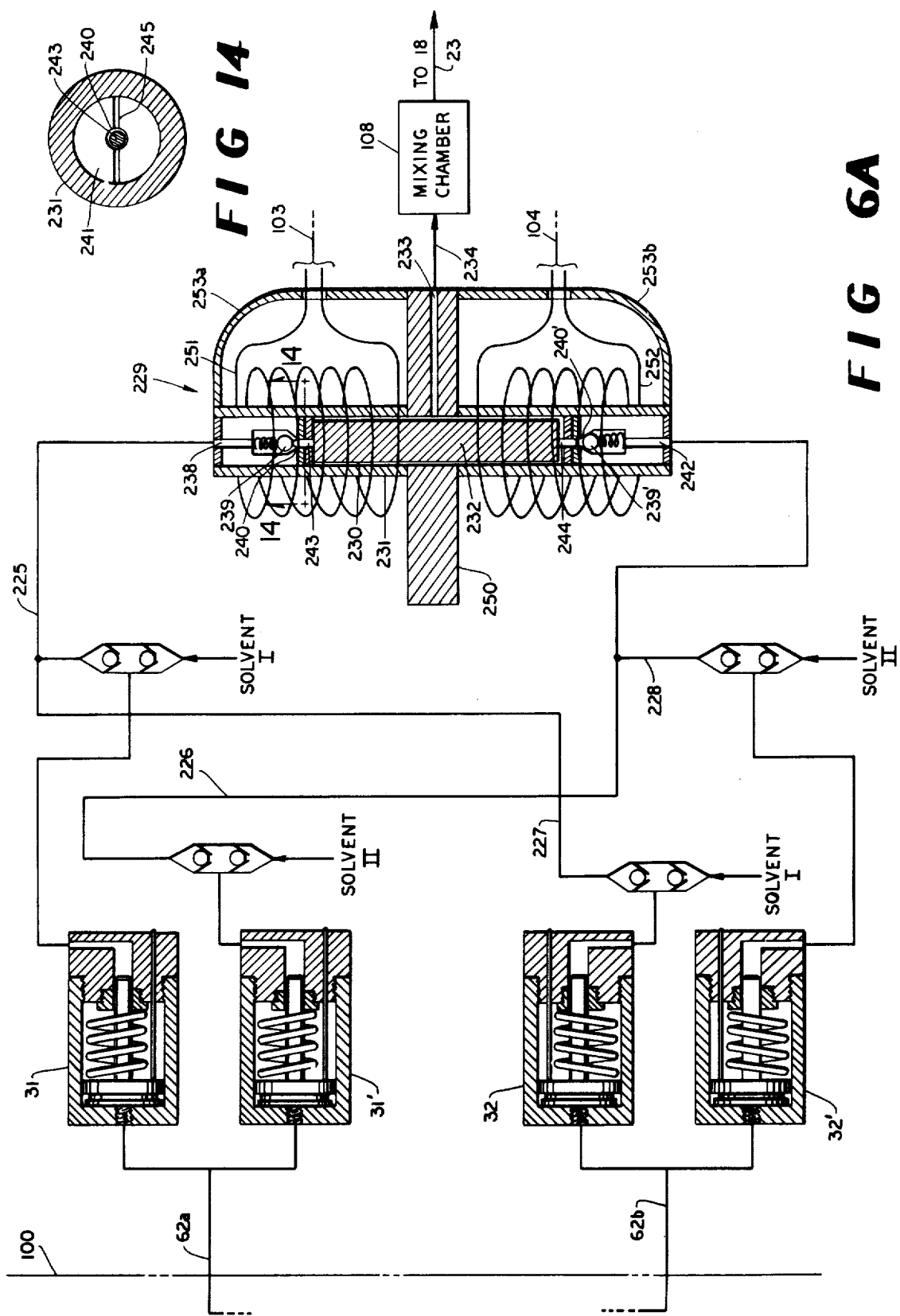
FIG. 6A is a block diagram of an alternative system for pumping two different carrier liquids according to the present invention.
FIG. 14 is a section view taken along line 14—14 of FIG. 6A.

FIG. 6A shows an alternative disclosed embodiment of apparatus for use of two different carrier liquids. Whereas the embodiment depicted in FIG. 6 accomplishes proportional delivery of two carrier liquids by selective operation of valves in the low-pressure input portion of the system, the alternative system depicted in FIG. 6A uses flow control in the high-pressure output portion to accomplish selective use of two carrier liquids. The low-pressure or hydraulic portion of the system depicted to the left of the line 100 in FIG. 6A is identical with the corresponding apparatus previously shown and described with reference to FIG. 6.

Pressurized operating liquid selectively applied to the line 62a is supplied in parallel to the two pressure intensifiers 31 and 31', which are respectively connected to pump solvent I and solvent II. The pressurized operating liquid selectively applied to the line 62b is similarly supplied in parallel to the input cylinders of the two pressure intensifiers 32 and 32', respectively connected to pump solvent I and solvent II. It will be understood that operating liquid in the line 62a, for example, is applied with equal operating force to each of the pressure intensifiers 31 and 31', thus causing the simultaneous pumping of solvent I through the line 225 and of solvent II through the line 226. It will also be apparent that operating liquid in the line 62b causes concurrent pumping of solvent I through the line 227 and of solvent II through the line 228.

Proportional selection of the solvents I and II is accomplished, in the embodiment depicted in FIG. 6A, through the use of a proportioning valve indicated generally at 229. The proportioning valve 229 includes a cylinder 230 which is defined by a tubular member 231. A valve shuttle 232 is reciprocably received within the cylinder 230, and the diameter of the shuttle 232 is sufficiently less than the diameter of the cylinder to permit solvent to flow in the annular space between the cylinder and the valve shuttle; a flow passage 233 extends in communication with the annular space and is connected by the line 234 to the mixing chamber 108, described below.

Solvent I is pumped along the lines 225 and 227 to enter the proportioning valve at a first inlet 238 in communication with a one-way valve 239 biassed in flow-blocking relation against an opening 240 (FIG. 14). Solvent II is similarly applied at the second inlet 242 of the proportioning valve, through a one-way valve 239' and an opening 240'.

The valve shuttle 232 has a first operating member 243 extending outwardly from the shuttle in axial alignment with the opening 240, and has a second operating member 244 extending from the opposite end of the shuttle in axial alignment with the opening 240'. The longitudinal extent of the valve shuttle 32, including the first and second operating members 243 and 244, is selected to ensure that at least one of the one-way valves 239 and 239' will always be maintained at least partially unseated by a corresponding operating member, so that no position of the valve shuttle exists which allows both of the one-way valves 239 and 239' to be simultaneously completely closed to block solvent flow.

As best seen in FIG. 14, the opening 240 is surrounded by a seat member 241 having a fluid flow channel 245 formed therein to allow solvent to flow through the opening 240 and the flow channel 245 notwithstanding abutment of the valve shuttle against the seat 241. A similar seat member and flow channel is provided in the valve seat 241'. The tubular member 31 defining the cylinder 230 is made of a suitable magnetically-permeable material and is divided at approximately a midpoint along the longitudinal extent of the tubular member by a barrier member 250, which is also made of a suitable magnetically-permeable material. A first control winding 251 is wound around the exterior of the first half of the tubular member 231, extending between the barrier 250 and the first inlet 238. A second control winding 252 is wound in a similar manner about the second half of the tubular member, extending between the barrier 250 and the second inlet end 242. Magnetic paths between the barrier 250 and the two ends of the proportioning valve are completed by the bridge members 253a and 253b, each of which is also made of a suitable magnetically permeable material. The first winding 251 is connected to receive control signals along the control line 103, while the second winding 252 is connected to receive control signals along the control line 104. It will be understood that the signals supplied along the control lines 103 and 104 are connected to a suitable source of proportional control signals as described above with respect to the embodiment depicted in FIG. 6.

Considering the operation of the embodiment depicted in FIG. 6A, it will be understood that application of a control signal to the first winding 251 causes the valve shuttle 232 to move toward the first inlet end 238 of the proportioning valve 229. It will also be understood that a control signal applied to the second winding 252 causes the valve shuttle 232 to move away from the first inlet end 238 and toward the second inlet end 242. Assuming that the first winding 251 is energized, the first operating member 243 of the valve shuttle maintains the one-way valve 239 open, allowing solvent I to flow from the pressure intensifier 31 (or 32) currently receiving hydraulic operating liquid, through the passage 233, and thence to the mixing chamber 108. After the passage of some predetermined time determined by the proportional control, the first winding 251 is deenergized and the second winding 252 becomes energized to shift the shuttle 232 to position whereat the first operating member 243 allows the one-way valve 239 to close and the second operating member 244 opens the one-way valve 239', allowing solvent II to enter the second inlet 242 of the proportioning valve. During the time that the second winding 252 is energized, accordingly, solvent II enters the proportioning valve through the second inlet 242 and flows through the passage 233 toward the mixing chamber 108.

The alternative embodiment of a solvent proportioning system, as depicted in FIG. 6A, provides fail-safe operation which cannot allow both flow circuits to be concurrently closed, because of the aforementioned design of the proportioning valve 229 to allow at least one of the one-way valves thereof to be at least partially opened. Moreover, the use of a single flow-switching element, such as the proportioning valve 229, provides a transition between liquid flow circuits which is less likely to cause unwanted pressure perturbations than is a switching system requiring separate valves in each flow line.

Although the proportioning valve 229, as described, is actuated by windings which require constant energization to maintain a valve position, those skilled in the art will recognize that the proportioning valve can alternatively be provided with a magnetic latch which maintains the valve shuttle in either operating position without requiring constant application of electrical power to a winding. Valve switching is accomplished with a momentary signal pulse, thereby avoiding the heating problems associated with coils which must be constantly energized.

Sample Introduction Valve

The illustrative embodiment of the sample introduction valve 18 is shown in FIGS. 7-9 and includes a unitary valve body 115 having a cylindrical chamber 116 extending from the end 117 a predetermined distance into the valve body. The innermost extent of the chamber 116 is defined by the annular plane surface 118, through which extends a shaft passage 119 coaxial with the centerline of the cylindrical chamber 116. A pair of ports 120 and 121 extend downwardly from the surface 118 and are respectively connected to the respective conduits 24 and 22. An additional port 125 extends into communication with the wall of the chamber at a location above the surface 18, as shown in FIG. 7. The valve body 115 may advantageously be machined or otherwise formed from a unitary block of metal or other material having suitable physical properties, including resistance to attack by the liquids flowing therethrough and sufficient structrual strength to withstand the operating pressures encountered.

A rotor 122 is received within the chamber 116 for rotation therein, and a rotor shaft 123 is connected to the rotor and extends downwardly through the shaft passage 119 for access at the other end 124 of the valve body 115. The rotor 122 has a peripheral surface 128 which is dimensioned to permit rotation of the rotor within the cylindrical chamber 116. The rotor 122, as particularly shown in FIG. 9, includes a pair of spaced-apart parallel faces 129a and 129b which are perpendicular to the rotational axis of the rotor. Four passages 130, 131, 132, and 133 extend through the thickness of the rotor 122 for communication between the two parallel faces. Each of the passages 130–133 has a preferably unique volume within the rotor 122 equal to a corresponding number of predetermined desired volumes of sample material to be introduced into the liquid chromatograph circuit; these passages may advantageously be formed by holes of appropriate diameter drilled through the thickness of the rotor 122. Each of the rotor faces 129a and 129b has an annular land 134a and 134b, respectively, surrounding the rotor axis. The passages 130–133 extend between and terminate at these lands, and it will become apparent that the lands and the corresponding confronting surfaces of the sample introduction valve are compressed together to establish a liquid sealing contact. The rotor 122 in an actual embodiment of the present invention is made of graphite-filled material such as polytetrafluoroethylene (commonly available under the trademark Teflon), although other suitable materials may be substituted by those skilled in the art.

The rotor 122 is retained in place within the chamber 116 by the compression cap 137, which is attached to the end 117 of the valve body 115 by suitable fasteners such as bolts or the like. The compression cap 137 includes an end portion 138 which covers and attaches to the end 117 of the valve body, and a closure portion 139 which is preferably formed integrally with the end portion and which extends into the chamber 116 of the valve body 115. The closure portion 139 has an end face 140 which is maintained in liquid sealing contact against the land 134a of the rotor 122, and the land 134b of the rotor is likewise maintained in liquid sealing contact with the surface 118 of the valve body 115. A pair of ports 141 and 142 extend through the compression cap 137 between the end face 140 and the outer surface of the compression cap 137, and the conduits 23 and 20 are respectively connected to these two ports. The ports 141 and 142 open onto the end face 140 at locations spaced 90° apart from each other, with reference to the axis of rotation of the rotor 122. It will be understood that the two ports 120 and 121 on the surface 118 are also spaced 180° apart from each other, and are positioned on the surface 118 to place the port 120 in axial alignment with the port 141 and to place the port 121 in axial alignment with the port 142. The passages 130–133 in the rotor 122 are positioned at 90° intervals about the rotor, and are radially spaced for selective alignment with the ports in the valve body and in the compression cap. It will be thus understood that any two angularly-adjacent rotor passages 130–133 may be concurrently aligned with the two ports in the valve body and in the compression cap, by rotation of the rotor shaft 123, to establish a first fluid flow path through the conduits 23 and 24, and to establish a concurrent second fluid flow path through the conduits 20 and 22.

Considering the operation of the sample introduction valve, and referring once again to the system flow diagram of FIG. 1, it can be seen that a flow of carrier liquid from the solvent reservoir 16 is maintained by the pumping system 17 through the conduit 23, the port 142, one of the rotor passages, the port 120, and the conduit 24 to the valve 25a and thence to the chromatograph column 15. Assuming that the rotor 122 is positioned to position the rotor passage 130 for the aforementioned carrier liquid flow, it will be seen that the rotor passage 131 is positioned between the ports 121 and 142 of the sample introduction valve. At this time, sample material from the sample source 21 can be introduced through the conduit 20 to fill the rotor passage 131. This flow of sample material can be induced by pressurizing the sample source 21, or by applying a partial vacuum to the conduit 22 by any suitable type of pump. Since the volume of the rotor passage 130 is a precisely predetermined volume corresponding to a desired sample volume, it is unnecessary to use a syringe or any other measuring instrument to meter the quantity of sample withdrawn from the sample source 21. It is merely necessary to observe the occurrence of sample material emerging from the conduit 22 to be assured that the rotor passage 131 is filled with the aforementioned predetermined volume of sample material.

After the rotor passage 131 is filled with sample material, the rotor shaft 123 can be rotated 90° to place the rotor passage 131 in alignment with the ports 120 and 141. The rotor passage 131 is thereby placed in communication with the flow of carrier liquid to the chromatograph column, and the sample material previously disposed in the rotor passage 131 is positively displaced by the carrier liquid flow to leave the rotor passage and to move toward the chromatograph column. Since the rotor passage 131 was entirely filled with sample material, no dead space is introduced into the chromatograph system along with the sample material. Moreover, the rotor passage 131 is swept clean of sample material by the continuing flow of carrier liquid through the passage and so this passage 131 is cleaned and made ready to receive another quantity of sample material upon being returned to a position aligned with the ports 121 and 142.

Each of the four passages in the rotor 122 preferably has a volume which is different from the volumes of the other rotor passages. For example, the four rotor passages can respectively have volumes of one, two, four, and eight microliters, thus providing the chromatograph user with four possible sample volumes merely by appropriate rotation of the rotor. The present sample valve permits any of such sample volumes to be selected and repeatably introduced into the chromatograph system, without errors of measurement resulting from the need to make separate measurements of each sample as in the prior art.

The rotor 122 also contains a passage extending from a port 135 in communication with the rotor face 129a to a port 136 in communication with the peripheral surface 128 of the rotor. The port 136 is spaced apart from the rotor face 129b a distance along the axis of the rotor which allows the port 136 to be selectively aligned with the port 125 on the cylindrical chamber 116 of the sample introduction valve. The angular position of the port 135 on the rotor face 129a is selected to place the port 135 in communication with the port 141 on the end face 140 of the compression cap 137, when the rotor 122 is angularly positioned to align the peripheral port 136 with the port 125 on the wall of the chamber 116. The port 125 is connected to a drain line 126 which can lead to a waste container or the like.

When the rotor 122 is angularly positioned to align the port 135 with the port 141, and the port 136 with the port 125, the flow of carrier liquid from the pumping system 17 is directly connected to the drain line 126. This connection is useful when a change is made in the carrier liquid being pumped, since the output cylinders of the pressure intensifiers will initially contain a quantity of the previously pumped carrier liquid. The pumping system is simply operated for at least one complete pumping cycle, enabling the previous carrier liquid to be flushed out of the pressure intensifiers directly through the drain line 126 without any substantial back pressure, so that the pumping system will not have to be flushed by the time-consuming technique of pumping the previous carrier liquid through the substantial back pressure presented by the chromatograph column.

Although the illustrative embodiment of the present sample valve includes a rotor having four separate passages, it will be understood by those skilled in the art that a greater or lesser number of rotor passages may alternatively be provided. The angular spacing between adjacent rotor passages, along with the angular spacing between the ports 141, 142 and the ports 120, 121, would be adjusted in accordance with the number of rotor passages.

Mixing Apparatus

The disclosed illustrative embodiment of the mixing chamber 108 is depicted in FIG. 10, where mixing of the intersperse segments of solvent (or of any other suitable liquids to be mixed) enters the chamber 150 defined by the interior walls of the enclosed cylinder 151. Received within the cylinder 150 is a mixing piston 152 of length less than the length of the cylinder 151 and configured to permit reciprocal movement of the mixing piston within the chamber 150.

A first portion 153 of the mixing piston 152 is of maximum piston diameter, and a second portion 154 is of reduced diameter; the diameter of the first portion 153 is selected to provide piston-cylinder clearance which is sufficient to allow the mixing piston to reciprocate within the chamber 150 without frictional contact with the cylinder wall, but which is sufficiently small to produce shear-effect flow of liquid around the first portion of the mixing piston, as the mixing piston reciprocates. A clearance of 0.010 inches between the first portion 153 of the mixing piston and the adjacent cylinder wall has provided satisfactory mixing of typical solvent liquids used in liquid chromatography.

A compression coil spring 157 surrounds the second portion 154 of the mixing piston and normally biases the mixing piston to one end of the chamber 150, as shown in FIG. 10. A solenoid coil 158 is contained within a housing 159 in surrounding relation with the opposite end of the cylinder 151 from where the mixing piston is normally biased by the spring 157. The mixing piston 151 is made of steel or another suitable magnetically permeable material, preferably encased in a coating of a suitable low-friction material such as Teflon or the like. It will be understood that the application of electrical power to the solenoid coil 158 establishes a magnetic field which urges the mixing piston 152 forward to become centralized within the solenoid coil, thereby overcoming the return bias of the spring 157. As soon as the solenoid coil is deenergized, the spring 157 returns the mixing piston to the position depicted in FIG. 9.

The cylinder 151 may be fabricated from a unitary piece of suitable material, thereby minimizing the requirement for sealed interconnections. Since the cylinder must have an open end for assembly of the piston-spring arrangement, the open end is provided with appropriate closure structure such as the cap 160 and collar 161 for securely sealing the open end of the cylinder.

In operation of the described mixing apparatus, the operating power supplied to the solenoid coil 158 is interrupted at a pulse rate which is sufficient, in consideration of the viscosity of liquid flowing into the chamber 150, to enable the mixing piston 152 to undergo a substantially complete forward stroke for each actuation of the solenoid, and to undergo a substantially complete return stroke during the time that the solenoid coil remains deenergized. The aforementioned piston-cylinder clearance between the first portion of the mixing piston and the surrounding cylinder causes the liquid in the chamber 150 to flow past the reciprocating mixing piston at a high velocity. The liquid flowing past the mixing piston at high velocity suddenly enters the larger volume existing behind the end of the moving piston and loses the high velocity flow, thereby creating a turbulent mixing effect on alternate sides of the reciprocating mixing piston. The liquid inflow to the mixing assembly 108, which in the disclosed embodiment consists of alternate segments of two different solvents, is thus effectively intermixed to provide a substantially homogenous liquid outflow along the conduit 23 to the remainder of the chromatograph system. The volume of the chamber swept by each reciprocation of the mixing piston is preferably large enough to contain at least one segment of each liquid being mixed.

Sample Recycling

The illustrative embodiment of sample recycling apparatus according to the present invention is described with reference to FIG. 1. In typical liquid chromatograph apparatus, the liquid flows from the chromatograph column to a suitable detector, after which the liquid is subsequently drained or otherwise removed from the chromatograph system. The liquid outflow from the detector 19 of the present system, however, is connected by the conduit 165 to the two-way valve 166. The two-way valve 166 selectively connects the conduit 165 with either of the output conduits 167 or 168. Conduit 167 serves as a conventional drain line to receive the liquid outflow from the detector 19 during conventional operation of the chromatograph.

The conduit 168 is connected to a first input of another two-way valve 169. A second input of the two-way valve 169 is connected by the conduit 170 to an output of the recycle selection valve 25a. The common output line of the two-way valve 169 is connected to the input of the recycling loop 171, and the output of the recycling loop is connected with the conduit 172 to an input of the recycle selection valve 25b.

The recycling loop 171 is a location for the temporary storage of a segment of liquid outflow from the detector 19. The recycling loop 171 may be provided most simply by a length of conduit having appropriate inner diameter and length to provide the desired storage volume.

Considering the operation of the present recycling system, those skilled in the art will recognize that the ability of a liquid chromatograph to identify the constituents of a sample depends, among other things, upon the length of the chromatograph column. Practical limitations on the maximum length of the column may permit only incomplete separation of two or more constituents of a sample, with the result occurring at detector output as a single gross signal indication rather than as a series of separate signal maxima corresponding to separate constituent ingredients.

It has been determined that a portion of sample material which has passed through the chromatograph can be subject to chromatographic analysis in expanded detail if the sample portion is readmitted to the head of the chromatograph column and once again passed through the column. In this manner, a sample portion which once occupied only a portion of the column length now has available the entire length of the column, with the result that the individual constituents of the sample are more readily detected in the outflow from the column as separate peaks on the detector output.

Assuming that the system of FIG. 1 is operating in a normal manner, the recycle selection valve 25a and 25b and the two-way valve 166 are all in the position shown by solid lines in FIG. 1. Carrier liquid and sample material passes along the conduit 24, through the valves 25a and 25b, and into the chromatograph column 15. Subsequently, the liquid outflow from the chromatograph column passes through the detector 19 and through the valve 166 to the drain conduit 167. If the operator of the chromatograph system desires to obtain an additional analysis of a particular sample portion, the two-way valve 166 is operated to place the conduit 165 in communication with the conduit 168 and the two-way valve 169 (presently in the solid-line position shown in FIG. 1). The outflow from the detector 19 is thus loaded into the recycling loop 171.

After the recycling loop is loaded, the two-way valve 166 can be returned to the normal position to permit continued operation of the chromatograph. The operator of the chromatograph system at this time may continue the normal operation as aforementioned, or may alternatively place the valves 25a, 25b, and 169 in the broken-line positions shown in FIG. 1. The flow of carrier liquid in the conduit 24 is diverted into the conduit 170 and is applied to the input of the recycling loop 171 to displace the previously loaded sample portion into the conduit 172 and through the valve 25b to enter the chromatograph column 15. It will be thus seen that the material previously loaded into the recycling loop is reintroduced into the chromatograph column, and the sample portion which previously occupied only a portion of the column now has available the entire length of the column.

After the material is removed from the recycling loop 171, the valves 25a and 25b may again be operated to establish normal operation of the chromatograph system.

Improved Detector Apparatus

Figure 11:
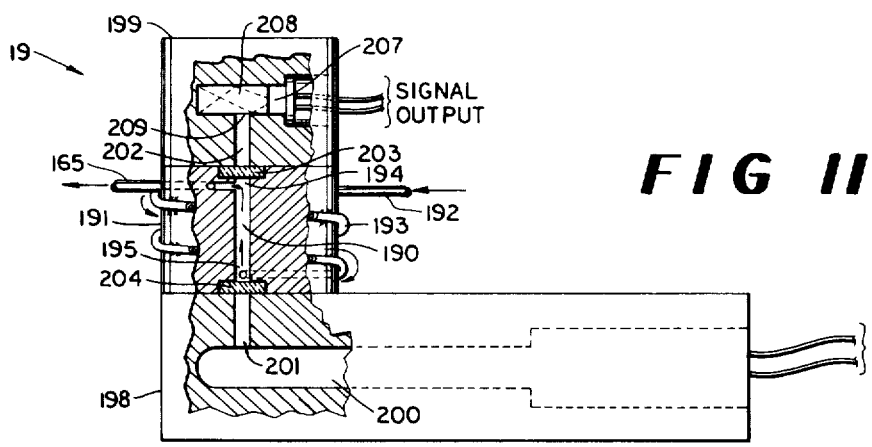
FIG. 11 is a partially broken-away and sectioned view of an improved detector apparatus according to a disclosed illustrative embodiment of the present invention.

An embodiment of the improved detector apparatus 19 is shown in FIG. 11, and includes a linear elongated sample cell 190 through which the liquid from the chromatograph column flows. The sample cell 190 in the disclosed embodiment is provided by a passage extending through a sample block 191 which, in order to provide substantial thermal inertia, is preferably made of a metal which is not reactive in the presence of the liquid stream from the chromatograph column. The sample block 191 preferably has a cylindrical exterior configuration, and the line 192 carrying liquid from the chromatograph column is wound around the exterior of the sample block as indicated at 193 to enhance the thermal equilibrium in the detector apparatus. The line 192 is preferably metallic tubing which is secured in good heat transfer relation to the sample block. Securing techniques such as welding, soldering, or the like can be used to secure the windings 193 to the sample block. A first end 195 of the sample cell 190 is connected to receive fluid flowing from the line 192, and a second end 194 of the sample cell is connected to the exit line 165.

Positioned on opposite sides of the sample block 191 are a lamp housing 198 and a detector cell housing 199. The lamp housing 198 contains an ultraviolet lamp (omitted in FIG. 11 for clarity) within a receptacle 200, and a narrow elongated passageway 201 extends from the lamp housing in coaxial alignment with the sample cell 190 to direct a substantially collimated beam of ultraviolet illumination into the sample cell. The detector cell housing 199 includes an elongated linear passageway 202 coaxially aligned with the passageway 201 and the sample cell 190. A pair of windows 203 and 204 are positioned at the two ends of the sample cell 190 to enclose the sample cell. The windows 203 and 204 should be of a material such as sapphire or the like, which has little or no absorption of ultraviolet illumination.

The ultraviolet illumination passing through the sample cell 190, and the liquid sample flowing therethrough, passes along the passageway 202 and impinges an illumination converter and multiplier element 208 positioned in the detector cell housing 199. The element 208, which is made of fluorescent glass or another suitable material capable of converting received ultraviolet illumination into visible illumination, has a substantially flat surface 209 positioned substantially perpendicular to the longitudinal axis of the passageway 202, so that the substantially collimated ultraviolet illumination in the passageway 202 impinges the element 208 at substantially a right angle thereto.

The photodetector device 207, which is any device such as a photocell or the like that provides an output signal in response to the magnitude of impinging visible illumination, is positioned in the detector cell housing 199 in laterally offset relation to the passageway 202, and with the illumination inlet aperture of the device 207 being in perpendicular relation to the longitudinal axis of the passageway 202. However, the depicted perpendicular relation between the photodetector device 207 and the passageway 202 is not considered critical.

Although the beam of ultraviolet illumination which strikes the element 208 is substantially collimated by passage through the coaxial passageway 201, the sample cell 190, and the passageway 202, the photons of visible illumination provided by the element 208 in response to such ultraviolet illumination move in directions having no correlation with the collimated direction of the incoming ultraviolet illumination. The visible illumination produced by the element 208 is uncollimated, as a consequence. The sensitivity of the detector apparatus 19 is substantially improved by providing the element 208 to be internally reflective of the visible light produced in response to ultraviolet illumination, so that substantially all of such visible light is internally reflected until the visible light impinges the photodetector device 207. The internal reflection of visible illumination within the element 208 is provided by the total reflection of visible light which internally impinges a surface of the element at less than the critical angle, and this internal reflection can be enhanced by adding a suitable reflective coating to the exterior surface of the element (except for the surface 209 and the interface between the element 208 and the photodetector device 207).

Those skilled in the art will recognize that a complete detection system includes not only the sample cell 190, shown in FIG. 11, but additionally includes a reference cell to provide a reference signal against which the variable signal output of the photodetector device 207 is compared. Moreover, the sample cell and the reference cell are connected with appropriate electronic circuits, such as a bridge circuit, to provide the aforementioned comparison, and the comparison output signal may be applied to suitable indicators or recorders to provide a graphical representation of the chromatograph output. The reference cell may be of identical construction to the sample cell shown in FIG. 11, with the exception that liquid from the column does not flow through the sample cell. The sample cell may contain either air or pure carrier liquid, as is known to those skilled in the art.

It will be apparent that the foregoing relates only to disclosed embodiments of the present inventions, and that numerous alterations and modifications may be made therein without departing from the spirit and the scope of he inventions as defined in the following claims.

What is claimed is:

1. Apparatus for measuring a certain volume of material and selectively introducing the measured volume into a fluid stream, comprising:
   a valve body;
   a valve member selectively movably received in said valve body, said valve member having a first fluid flow passage therein;
   said first fluid flow passage having a precisely defined volume equal to the certain volume to be measured;
   a first fluid flow circuit in said valve body;
   a second fluid flow passage in said valve member;
   a second fluid flow circuit in said valve body;
   said second fluid flow passage being located in said valve member to be in fluid flow alignment with said second flow circuit when said valve member is positioned in the sample measuring position placing said first fluid flow passage in said first fluid flow circuit;
   means selectively positioning said valve member either to a sample measuring position placing said fluid flow passage in said first fluid flow circuit, or to a sample introduction position placing said fluid flow passage in said second flow circuit;
   a third fluid flow passage located in said valve body to be in fluid flow alignment with an inlet portion of said second fluid flow circuit and with a bypass output line in said valve body, in response to selective rotation of said valve member to a bypass position; and
   means on said valve member interrupting said second fluid flow circuit when said valve body is in said bypass position.

2. Apparatus as in claim 1, wherein:
   said valve member comprises a rotor received for selective rotation within said valve body;
   said fluid flow passages extend in a generally axial direction through said rotor in angularly spaced apart relation thereon; and
   said first and second fluid flow circuits are interrupted by said rotor at locations thereon which enable said fluid flow passages to be placed in said measuring position and said introduction position by selective rotation of said rotor.

3. Apparatus as in claim 2, wherein:
   said rotor has a pair of spaced apart faces and each of said fluid flow passages extends in communication with each said face;
   said valve body has a rotor receptacle including a pair of spaced apart confronting faces which sealingly confront said rotor faces;
   said first flow circuit includes an inlet opening in one of said confronting faces and an outlet opening in the other of said confronting faces;
   said second flow circuit includes a first opening in said one confronting face and a second opening in said other confronting face; and
   said inlet and outlet openings of each said flow circuit being located for selective fluid flow alignment with either of said fluid flow passages in response to said selective rotation of said rotor.

4. Apparatus as in claim 2, including at least one other fluid flow passage extending through said rotor, said other fluid flow passage having a precisely defined volume equal to another certain volume to be measured, and said other fluid flow passage is located on said rotor for alignment in said sample measuring position at the same time that one of the first and second fluid flow passages in aligned in said sample introduction position.

* * * * *